United States Patent [19]

Kikuchi et al.

[11] Patent Number: 5,013,828

[45] Date of Patent: May 7, 1991

[54] PREPARATION OF DIACYL DERIVATIVES OF 2'-DEOXY-5-FLUOROURIDINE VIA NOVEL INTERMEDIATE COMPOUND

[75] Inventors: Yoshiyuki Kikuchi, Tokyo; Akihiro Ishii, Kawagoe, both of Japan

[73] Assignee: Central Glass Company, Limited, Ube, Japan

[21] Appl. No.: 342,350

[22] Filed: Apr. 21, 1989

[30] Foreign Application Priority Data

Apr. 21, 1988 [JP] Japan ................................. 63-96821
Apr. 25, 1988 [JP] Japan ................................ 63-102189

[51] Int. Cl.$^5$ ..................... C07H 19/06; C07D 239/54
[52] U.S. Cl. ........................................ 536/23; 544/313
[58] Field of Search ........................ 536/23; 544/313

[56] References Cited

U.S. PATENT DOCUMENTS

| | | |
|---|---|---|
| 2,949,451 | 8/1960 | Hoffer ................................... 536/23 |
| 3,168,513 | 2/1965 | Duschinsky .......................... 536/23 |
| 3,221,010 | 11/1965 | Duschinsky .......................... 536/23 |
| 3,870,700 | 3/1975 | Kotick et al. ......................... 536/23 |
| 4,022,963 | 5/1977 | Deutsch ................................ 536/23 |
| 4,122,251 | 10/1978 | Misaki et al. ......................... 536/23 |

FOREIGN PATENT DOCUMENTS

| | | |
|---|---|---|
| 257361 | 2/1988 | European Pat. Off. ............ 536/231 |
| 95001 | 1/1973 | German Democratic Rep. . |
| 55-40598 | 10/1980 | Japan . |
| 58-49315 | 3/1983 | Japan . |
| 62-47197 | 10/1987 | Japan . |

OTHER PUBLICATIONS

Hoffer et al, JACS, vol. 81, p. 4112 (1959).
Kawaguchi et al, Chem. Pharm Bull. 33(1) 301-307 (1985).
Kawaguchi et al, Chem. Pharm. Bull. 33(4) 1652-1659 (1985).
Vissar et al, J. Chem. Soc. Perkin Trans. I, 1988, p. 2547.
Duschinsky et al, Chem. Abst. 66,46550v (1967).
Ozaki et al, Chem. Abst. 87-201989z (1977).
Kanzawa et al, Chem. Abst. 95-197203j (1981).
Fujii et al., Chem. Abst. 96-123229w (1982).
Fujii et al, Chem. Abst. 96-123233t (1982).
Teikoku Kako Co. Ltd., Chem. Abst. 96-7036g (1982).
Mitsui Pharmaceuticals, Inc. Chem., Abst. 99-10862r (1983).
Ozaki et al, Chem. Abst. 100-210325u (1984).
Noyori et al, Chem. Abst. 107-154657j (1987).
Fujii et al, Chem. Abst. 109-6904p (1988).
Tsuchiya et al, Chem. Abst. 109-55175k (1988).

*Primary Examiner*—Cecilia Shen
*Attorney, Agent, or Firm*—Fleit, Jacobson, Cohn, Price, Holman & Stern

[57] ABSTRACT

2'-Deoxy-3',5'-diacyl-5-fluorouridines useful as antitumor medicines or intermediates thereof are easily and efficiently obtained by first fluorinating 2'-deoxyuridine in aqueous solution with fluorine gas to thereby form 2'-deoxy-5,6-dihydro-5-fluoro-6-hydroxyuridine, which is a novel compound, and reacting this compound with a carboxylic acid anhydride or halide R—CO—X, where R is an aliphatic group having not more than 20 carbon atoms or a substituted or unsubstituted phenyl group, and X is an acyloxy group $RCO_2$ or a halogen atom. In the initial fluorination reaction the aqueous solution may contain a carbonate (or a hydrogen carbonate) or a lower fatty acid or its salt to capture hydrogen fluoride formed by the reaction. The next acylating reaction can be promoted by carrying out the reaction in the presence of an organic base such as pyridine.

12 Claims, No Drawings

PREPARATION OF DIACYL DERIVATIVES OF 2'-DEOXY-5-FLUOROURIDINE VIA NOVEL INTERMEDIATE COMPOUND

BACKGROUND OF THE INVENTION

This invention relates to the preparation of 2'-deoxy-5-fluorouridine derivatives useful as antitumor medicines or intermediates thereof, and more particularly to the preparation of 2'-deoxy-3',5'-diacyl-5-fluorouridines from 2'-deoxyuridine via a novel intermediate compound.

2'-Deoxy-5-fluorouridine is a compound synthesized for use as an antitumor medicine, but actually this compound is high in toxicity and low in activity in the human body. To reduce toxicity and enhance antitumor activity, 2'-deoxy-5-fluorouridine derivatives such as 3',5'-diacyl derivatives (e.g. JP-A 58-49315) and 3-aroyl-3',5'-diacyl derivatives (e.g. JP 62-47197) have been developed. These derivatives are synthesized by acylating 2'-deoxy-5-fluorouridine by reaction with an acyl halide.

At present, however, 2'-deoxy-5-fluorouridine is very expensive and is not readily available because no industrially favorable method for the preparation of this compound has been developed.

Known processes of preparing diacyl derivatives of 2'-deoxy-5-fluorouridine include reducing a 2'-halogen derivative (JP 55-40598) and reacting fluorine gas with a diacyl derivative in an organic solvent (DDR Pat. No. 95001). However, the reduction process entails several steps to prepare the 2'-halogen derivative, and the fluorination in organic solvent is not easy to accomplish on an industrial scale.

SUMMARY OF THE INVENTION

It is an object of the present invention to provide a simple and industrially practicable process for efficiently preparing 3',5'-diacyl derivatives of 2'-deoxy-5-fluorouridine.

It is another object of the invention to provide a novel derivative of 2'-deoxyuridine from which 2'-deoxy-3',5'-diacyl-5-fluorouridines can easily be prepared.

To accomplish the above objects the present invention employs 2'-deoxyuridine, which is an industrially available material, as the starting material. We have discovered that fluorination of 2'-deoxyuridine in an aqeous solution gives a novel compound, viz., 2'-deoxy-5,6-dihydro-5-fluoro-6-hydroxyuridine, and that the novel compound can easily be acylated to 2'-deoxy-3',5'-diacyl-5-fluorouridines useful as antitumor medicines or intermediates thereof.

2'-Deoxy-5,6-dihydro-5-fluoro-6-hydroxyuridine is a compound of the following formula [A]. Hereinafter this compound will be referred to as compound [A].

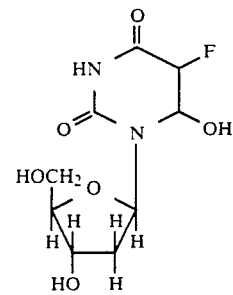

According to the invention, compound [A] is prepared by reacting fluorine gas with an aqueous solution of 2'-deoxyuridine.

In another aspect, the present invention is a process of preparing a diacyl derivative of 2'-deoxy-5-fluorouridine represented by the general formula (I),

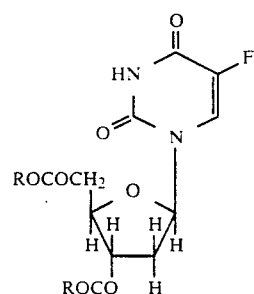

wherein R represents an aliphatic group having not more than 20 carbon atoms or a substituted or unsubstituted phenyl group, the method comprising the steps of (a) reacting fluorine gas with an aqueous solution of 2'-deoxyuridine to thereby form compound [A], and (b) reacting the compound [A] with a compound represented by the general formula (II), viz., a carboxylic acid anhydride or halide, $$R-CO-X \qquad (II)$$

wherein R is as defined above with respect to the general formula (I), and X is an acyloxy group represented by $RCO_2$ (where R is the same as R in the general formula (II)) or a halogen atom.

Furthermore, as a modification of the above process this invention provides another process of preparing a diacyl derivative of 2'-deoxy-5-fluorouridine represented by the general formula (I), the process comprising the steps of (i) fluorinating 2'-deoxyuridine in the form of an aqueous solution with fluorine gas in the presence of a fatty acid having not more than 4 carbon atoms or a salt of the fatty acid, and (ii) reacting a fluorinated intermediate formed at step (i) with a compound represented by the general formula (II).

The principal advantage of the invention resides in that 2'-deoxy-3',5'-diacyl-5-fluorouridines can be prepared from industrially available 2'-deoxyuridine at good efficiency by a simple process consisting essentially of fluorination of the starting compound in an aqueous solution and acylation of the fluorinated intermediate.

It is possible to efficiently obtain 2'-deoxy-5-fluorouridine by hydrolyzing a deacyl derivative prepared by a process according to the invention.

DESCRIPTION OF THE PREFERRED EMBODIMENTS

In an aqueous solution 2'-deoxyuridine is easily fluorinated into compound [A]. The concentration of 2'-deoxyuridine in the aqueous solution is not strictly limited, but in practice it is suitable that the concentration ranges from about 3 wt % to about 20 wt % because when the concentration is too low the apparatus must have an uneconomically large capacity. For the fluorination it is suitable to use diluted fluorine gas, viz., a mixed gas consisting of 5-20 mol % of fluorine gas and the balance of an inactive gas such as nitrogen, helium or argon.

The fluorination reaction proceeds smoothly. Since the reaction liquid becomes strongly acidic as the fluorination reaction proceeds, there is a possibility of formation of by-products attributed to the cleavage of the ribose-base bond in the uridine structure. To suppress the formation of such by-products it is suitable to carry out the fluorination reaction at temperatures not higher than 50° C., and preferably at temperatures ranging from 0° to 25° C. Also for suppressing the formation of by-products it is effective to use an aqueous solution containing a water soluble carbonate or hydrogen carbonate such as sodium (hydrogen) carbonate or potassium (hydrogen) carbonate because the carbonate or hydrogen carbonate captures HF formed by the fluorination reaction. It is suitable to use at least 1 mol of a carbonate or hydrogen carbonate per mol of 2'-deoxyuridine.

After completion of the fluorination reaction it is preferable to neutralize the reaction liquid with a suitable salt such as calcium carbonate to prevent the decomposition of the reaction product by heating in the subsequent isolation process.

The compound [A] has 1 mol of water of hydration and is obtained as a white powder having a melting point of 40°-45° C.

From compound [A] a 2'-deoxy-3',5'-diacyl-5-fluorouridine can easily be derived. That is, acylation of compound [A] at the 3'- and 5'-positions and elimination of —OH group at the 6-position are readily accomplished by mild heating of a mixture of compound [A] and a carboxylic acid anhydride or halide represented by the general formula (II). It is suitable to use at least 4 mols of acid anhydride or halide per mol of compound [A].

In the case of using an acid anhydride, it can be selected from not only straight-chain or branched anhydrides such as acetic anhydride, propionic anhydride and isobutyric anhydride but also cyclic anhydrides represented by succinic anhydride. When a cyclic anhydride is used, a carboxyl substituted diacyl derivative of 2'-deoxy-5-fluorouridine is obtained. In the case of using an acid halide, it can be selected from not only aliphatic carboxylic acid halides such as acetyl chloride, acetyl bromide, caprylyl chloride and lauroyl chloride but also aromatic carboxylic acid halides such as benzoyl chloride and p-chlorobenzoyl chloride.

Usually the acylating reaction is carried out at a temperature ranging from room temperature to 120° C., though this is not limitative. Purification of the reaction product in the aqueous reaction system is accomplished by removing water under reduced pressure and subjecting the solid residue to column chromatography and/or recrystallization.

For promotion of the acylating reaction it is effective to add an organic base to the mixture of compound [A] and a carboxylic acid anhydride or halide. For example, the organic base is selected from pyridine, substituted pyridines, N-alkylimidazoles, trialkylamines and N,N-dialkylcarboxylic acid amides. The amount of the organic base is arbitrary: it may be as small as about 5 mol % of compound [A] or large enough to serve as a liquid medium for the reaction.

In the acylating reaction it is optional to use an organic solvent in which the reactants are soluble, such as ethyl acetate, acetonitrile or tetrahydrofuran.

In fluorinating 2'-deoxyuridine in aqueous solution with diluted fluorine gas it is optional to add a lower fatty acid (having not more than 4 carbon atoms) such as formic acid, acetic acid, propionic acid or butyric acid, or a salt of the fatty acid, to the aqueous solution. In the case of using an acid salt, it can be selected from alkali metal salts such as lithium salt, sodium salt and potassium salt, alkaline earth metal salts such as magnesium salt and barium salt and ammonium salts. The added fatty acid or its salt captures HF formed by the fluorination reaction and, besides, serves a catalytic function in the subsequent acylating reaction. To fully obtain such effects it is suitable to use at least 1 mol, and preferably 2 to 5 mols, of fatty acid or its salt per mol of 2'-deoxyuridine. In this case it is preferable that the concentration of 2'-deoxyuridine in the aqueous solution is not higher than 10 wt %.

In the aqueous solution containing a fatty acid or its salt the fluorination of 2'-deoxyuridine proceeds without need of heating. To suppress the cleavage of the ribose-base bond it is suitable to carry out the reaction at temperatures ranging from 0° C. to room temperature. The progress of the reaction may be traced by high speed liquid chromatography to terminate the introduction of fluorine gas into the aqueous solution when the starting compound vanishes.

In the presence of a fatty acid or its salt, the fluorination reaction of 2'-deoxyuridine gives a mixture of 2'-deoxy-5,6-dihydro-5-fluoro-6-hydroxyuridine (compound [A]) and a 2'-deoxy-5,6-dihydro-5-fluoro-6-acyloxyuridine, as represented by the following reaction formula by way of example.

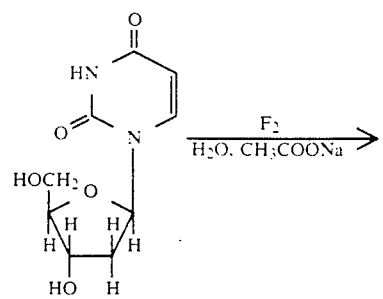

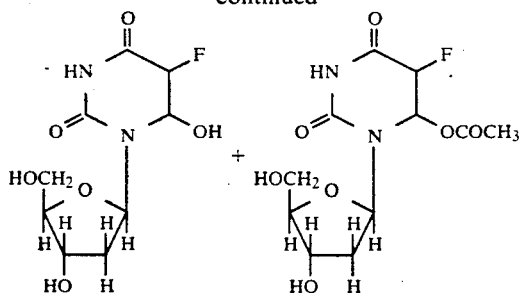

In the fluorinated mixture, the proportion of compound [A] to the 6-acyloxy derivative varies depending on the quantity of and the carbon number of the added fatty acid or its salt.

After completion of the fluorination reaction water is removed under reduced pressure, and the solid residue is dried. The solid residue is the aforementioned mixture of the fluorinated derivatives. The solid residue is subjected to the second-stage reaction by adding thereto a carboxylic acid anhydride or halide represented by the general formula (II) and heating the resultant mixture under stirring. It is suitable to use 4 to 50 mols of acid anhydride or halide per mol of the fluorinated intermediate mixture or per mol of the starting 2'-deoxyuridine. Examples of suitable acid anhydrides and halides are as described hereinbefore. The reaction is carried out at temperatures ranging from room temperature to the boiling point of the employed acid anhydride or halide. Considering both the rate of reaction and the suppression of side reactions, a preferred range of the reaction temperature is from 50° to 120° C. The reaction is traced by high speed liquid chromatography to terminate heating when the materials in the reaction system ceases from changing. Also in this case it is effective to add an organic base such as, for example, pyridine to the reaction system for promotion of the acylating reaction.

For isolation of a 2'-deoxy-3',5'-diacyl-5-fluorouridine formed by the acylating reaction, the reaction product is transferred into water by diluting the reaction liquid with water or by first removing liquid under reduced pressure and then adding water to the solid residue and then extracted with a halogenated solvent such as chloroform, dichloromethane, 1,1,2-trichloroethane or tetrachloroethane. By distilling out the solvent a 2'-deoxy-3',5'-diacyl-5-fluorouridine is obtained as a palely colored crystalline or oil-like substance. According to the need the product can be refined by recrystallization.

As mentioned hereinbefore, 3',5'-diacyl derivatives of 2'-deoxy-5-fluorouridine are useful as antitumor medicines for example. Also it is possible to convert these diacyl derivatives into 2'-deoxy-5-fluorouridine by accomplishing deacylation by reaction with either an alkali metal hydroxide or ammonia in a hydrate alcohol. The deacylated 2'-deoxy-5-fluorouridine can be converted into different derivatives with asymmetric substitutions at the 3'- and 5'-positions to provide antitumor medicines having high effect.

The invention is further illustrated by the following nonlimitative examples.

EXAMPLE 1

To prepare compound [A], 50.0 g (0.22 mol) of 2'-deoxyuridine was dissolved in 1 liter of water. Vigorously stirring the aqueous solution, a mixed gas of 90 mol % He and 10 mol % $F_2$ was passed through the solution at a flow rate of 140 ml/min while the temperature of the solution was maintained at 3°–5° C. The fluorination reaction was traced by high speed liquid chromatography. It took 6 hours and 50 minutes to completely consume the starting material, and the total amount of $F_2$ consumed in the reaction was 0.236 mol.

After that the reaction liquid was neutralized by adding 31 g of calcium carbonate and stirring the resultant mixture for 1.5 hr. A white precipitate occurred by this treatment was removed by filtration through a celite layer. Next, under reduced pressure water was distilled out of the solution while maintaining the interior temperature below 40° C. to thereby obtain a viscous oil-like substance. The oil-like substance was dissolved by the addition of 200 ml of ethanol, and insoluble matter (white precipitate) was filtered out. Then, under reduced pressure the solvent was removed from the filtrate to thereby obtain 60.8 g of a white solid product, which was monohydrate of compound [A] (will be referred to as [A].$H_2O$). The yield was 98%. Analysis of this product gave the following results.

m.p.: 40°–45° C.

$^1$H-NMR (CD$_3$OD): δ2.25 (m, 2H, 2'—CH$_2$); 3.60-3.90 (m, 3H, 4'—CH, 5'—CH$_2$); 4.35 (m, 1H, 3'—CH), 5.27 (m, 1H, 5'—CH); 5.55 (m, 1H, 6—CH), 6.20 (t, 1H, 1'—CH).

$^{19}$F-NMR (CD$_3$OD): −7.2 (d, J=48 Hz); −5.0 (d, J=48 Hz), 9.6 (d, J=48 Hz); 12.4 (d, J=48 Hz) ppm (standard: CFCl$_3$).

Elementary Analysis: Found (wt %): C 38.30, H 5.38, N 9.63; Calculated (wt %): (as C$_9$H$_{13}$FN$_2$O$_6$.H$_2$O) C 38.40, H 5.12, N 9.32.

A portion of the obtained [A].$H_2O$ was treated with acetic anhydride in the presence of pyridine (in the manner as described in the subsequent Example 5) for conversion into 2'-deoxy-3',5'-diacetyl-5-fluorouridine. By a search made by high speed liquid chromatography it was found that the obtained derivative contained 1% of 5-fluorouracil resulting from cleavage of the ribose-base bond.

EXAMPLE 2-4

In these examples the process of Example 1 was repeated except that the fluorination reaction was carried out at a different temperature in Example 2 and with use of a carbonic additive in Examples 3 and 4. The particulars are shown in Table 1.

TABLE 1

|  | Fluorination Reaction | | Yield of [A].H$_2$O | Cleavage of Ribose-base Bond |
|---|---|---|---|---|
|  | Temperature | Additive |  |  |
| Ex. 2 | 25° C. | — | 87% | 3.8% |
| Ex. 3 | 3–5° C. | NaHCO$_3$, 0.44 mol | 70.5% | — |
| Ex. 4 | 3–5° C. | Na$_2$CO$_3$, 0.44 mol | 82.5% | — |

The following Examples 5 to 20 relate to acylation of compound [A].

EXAMPLE 5

First 4.47 g (15.9 mmol) of [A].$H_2O$ obtained in Example 1 was suspended in 40 g (0.39 mol) of acetic anhydride, and then 120 mg (1.56 mmol) of pyridine was added, and the mixture was stirred for 15 hr while maintaining the temperature at 100° C. Then the liquid was almost completely evaporated under reduced pressure, and the residue was subjected to recrystallization from ethanol to thereby obtain 3.80 g of 2'-deoxy-3',5'-diacetyl-5-fluorouridine, viz. a diacyl derivative represented by the general formula (I) (R is $CH_3$). The yield of the diacyl derivative was 72.6%. Analysis of the product gave the following results.

m.p.: 148°–149° C.

$^1$H-NMR (CDCl$_3$): δ2.15 (s, 6H), 2.2–2.8 (m, 2H); 4.3 (m, 3H), 5.2 (m, 1H), 6.3 (t, 1H); 7.65 (d, 1H, J=6 Hz).

$^{19}$F-NMR (CDCl$_3$): −164.88 ppm (d, J=5.9 Hz); (standard: CFCl$_3$).

IR (KBr): 3500, 1750, 1700, 1660, 1230 cm$^{-1}$.

EXAMPLES 6–10

In every example 1.00 g (3.6 mmol) of [A].H$_2$O was suspended in 9.7 g (89 mmol) of acetic anhydride, and a catalytic amount (0.32 mmol) of a selected organic base was added, and the mixture was stirred for several hours at a predetermined temperature. The particulars are shown in Table 2. In every case the reaction product was treated in the same manner as in Example 5 to thereby obtain 2'-deoxy-3',5'-diacetyl-5-fluorouridine.

TABLE 2

|  | Organic Base | Reaction Conditions Temp. (°C.) | Time (hr) | Yield of derivative (I) (R: CH$_3$) |
|---|---|---|---|---|
| Ex. 6 | 4-dimethylamino-pyridine | 70 | 4.6 | 80% |
| Ex. 7 | 4-picoline | 100 | 6 | 74% |
| Ex. 8 | N-methylimidazole | 70 | 6 | 81% |
| Ex. 9 | triethylamine | 70 | 11.6 | 79% |
| Ex. 10 | N,N-dimethyl-acetamide | 100 | 16 | 21% |

EXAMPLE 11

A mixture of 1.01 g (3.56 mmol) of [A].H$_2$O, 12.4 g (95.4 mmol) of propionic anhydride and 39 mg (0.32 mmol) of 4-dimethylaminopyridine was stirred at 70° C. for 2.5 hr. Then the liquid was distilled out under reduced pressure. The residue was recovered by adsorption by silica gel columu chromatography. Using benzene-methanol (5:1) mixture the aimed product was dissolved out of the adsorbed matter, and the dissolved product was purified by recrystallizing from ethanol-benzene. Obtained by this process was 0.78 g (yield 61%) of white crystals of 2'-deoxy-3',5'-dipropionyl-5-fluorouridine (R in the general formula (I) is C$_2$H$_5$). The melting point of this product was 78°–78.5° C.

EXAMPLE 12

A mixture of 1.00 g (3.55 mmol) of [A].H$_2$O, 14.0 g (88.6 mmol) of isobutyric anhydride and 39 mg (0.32 mmol) of 4-dimethylaminopyridine was stirred at 70° C. for 2.5 hr. Then the liquid was distilled out under reduced pressure. The residue was recovered by adsorption by silica gel column chromatography, and the aimed product was dissolved out by using chloroform-ethanol (60:1) mixture. The dissolved product was purified by recrystallization. Obtained was 1.05 g (yield 77%) of 2'-deoxy-3',5'-diisobutyryl-5-fluorouridine (R in the general formula (I) is C$_4$H$_9$). The melting point of this product was 121°–121.5° C.

EXAMPLE 13

In 17 ml of ethyl acetate, 1.02 g (3.6 mmol) of [A].H$_2$O, 8.9 g (89 mmol) of succinic anhydride and 39 mg (0.32 mmol) of 4-dimethylaminopyridine were refluxed for 5 hr under continuous stirring. Then the liquid was distilled out, and the residue was recovered by silica gel column chromatography. Using chloroform-ethanol (93:7) mixture the aimed product was dissolved out of the adsorbed matter, followed by purifying recrystallization. The purified product was 1.15 g (yield 73%) of 3',5'-bis(3-carboxypropionyl)-2'-deoxy-5-fluorouridine (R in the general formula (I) is $CH_2CH_2COOH$), which was an oil-like liquid. Analysis of the product gave the following results.

$^1$H-NMR ((CD$_3$)$_2$CO): δ2.10–2.70 (m, 10H), 4.10–4.50 (m, 3H); 5.10–5.40 (m, 1H), 6.25 (t, 1H, J=6.8 Hz); 7.75 (d, 1H, J=6.8 Hz), 4.90–6.10 (brood).

$^{19}$F-NMR ((CD$_3$)$_2$CO): −166.27 ppm (d, J=6.8 Hz); (standard: CFCl$_3$).

IR (Neat): 3500, 3250, 1740, 1490, 1290, 1180- - - cm$^{-1}$.

EXAMPLE 14

Stirring a solution of 1.18 g (4.2 mmol) of [A].H$_2$O in 24 ml of pyridine at 0° C., 4.76 g (29.3 mmol) of caprylyl chloride was dropped into the solution. After that the solution was kept heated at 95° C. and stirred for 5 hr. Then the reaction liquid was poured into water, and the reaction product was extracted with chloroform. The extract was washed with diluted sulfuric acid, 1% aqueous solution of sodium hydrogen carbonate and water in turn and dried by magnesium sulfate. The remaining solvent was distilled out, and the residue was recovered by silica gel column chromatography and dissolved in chloroform-n-hexane mixture (1:1), followed by purification. The product was 1.35 g (yield 65%) of 2'-deoxy-3',5'-dicaprylyl-5-fluorouridine (R in the general formula (I) is $(CH_2)_6CH_3$), which was an oil-like liquid. Analysis of the product gave the following results.

$^1$H-NMR (CDCl$_3$): δ0.90 (t, 6H, J=6 Hz); 1.10–2.00 (m, 20H), 2.00–2.90 (m, 6H); 4.10–4.70 (m, 3H), 5.10–5.40 (m, 1H); 6.35 (t, 1H, J=6 Hz), 7.70 (d, 1H, J=6.4 Hz); 9.90–10.70 (brood. s. 1H).

$^{19}$F-NMR (CDCl$_3$): −164.62 ppm (d, J=6.4 Hz); (standard: CFCl$_3$).

IR (KBr): 3240, 3120, 2960, 2890, 1740, 1480, 1370, 1280, 1180, 1120 cm$^{-1}$.

EXAMPLES 15–20

In each of these examples 1.0 g (3.6 mmol) of [A].H$_2$O was dissolved in 24 ml of pyridine, and 21.6 mmol of a selected acyl halide was added to the solution to carry out an acylation reaction under the same conditions as in Example 14, and the reaction product was treated in the same manner as in Example 14. In each case a crystalline diacyl derivative represented by the general formula (I) was obtained. The particulars are shown in Table 3, wherein Ph represents phenyl or phenylene group.

TABLE 3

|  | Acyl Halide | Obtained Acyl Derivative (I) R | Yield (%) | m.p. (°C.) |
|---|---|---|---|---|
| Ex. 15 | CH$_3$COCl | CH$_3$ | 80 | 148–149 |
| Ex. 16 | CH$_3$COBr | CH$_3$ | 82 | 148–149 |
| Ex. 17 | C$_2$H$_5$COCl | C$_2$H$_5$ | 91 | 73–73.5 |
| Ex. 18 | CH$_3$(CH$_2$)$_{10}$COCl | CH$_3$(CH$_2$)$_{10}$ | 32 | 49–50 |
| Ex. 19 | Ph—COCl | Ph | 39 | 246 |
| Ex. 20 | Cl—Ph—COCl | Cl—Ph— | 64 | 195–196 |

The following Examples 21 to 28 relate to the fluorination of 2'-deoxyuridine in the presence of a fatty acid or its salt and acylation of the fluorinated intermediate.

represented by the general formula (I) was obtained. The particulars are shown in Table 4.

TABLE 4

|  | Fatty Acid Salt | Ratio of 6-hydroxy to 6-acyloxy in fluorinated intermediates | Acid Anhydride | Final Product (I) | |
|---|---|---|---|---|---|
|  |  |  |  | R | yield |
| Ex. 22 | $CH_3CO_2Na$ (31.7 mmol) | 53/47 | $(CH_3CO_2)_2O$ | $CH_3$ | 87% |
| Ex. 23 | $CH_3CO_2K$ (17.6 mmol) | 63/37 | " | $CH_3$ | 90% |
| Ex. 24 | $(CH_3CO_2)_2Mg$* (17.6 mmol) | 62/38 | " | $CH_3$ | 74% |
| Ex. 25 | $(CH_3CO_2)_2Ba$ (17.6 mmol) | 71/29 | " | $CH_3$ | 36% |
| Ex. 26 | $CH_3CO_2NH_2$ (8.8 mmol) | 71/29 | " | $CH_3$ | 36% |
| Ex. 27 | $C_2H_5CO_2Na$ (17.6 mmol) | 88/12 | $(C_2H_5CO)_2O$ | $C_2H_5$ | 65% |
| Ex. 28 | $C_3H_7CO_2Na$ (17.6 mmol) | 99/1 | $(C_3H-CO)_2O$ | $C_3H_7$ | 77% |

*tetrahydrate

EXAMPLE 21

Together with 1.44 g (17.6 mmol) of sodium acetate, 2.02 g (8.80 mmol) of 2'-deoxyuridine was dissolved in 40 ml of water, and stirring the solution a mixed gas of 90 mol % of He and 10 mol % of $F_2$ was passed through the solution while the temperature of the solution was maintained at 3°–5° C. The fluorination reaction was traced by high speed liquid chromatography to detect that 2'-deoxyuridine was completely consumed as the total amount of consumed $F_2$ reached 11 mmol. Then the reaction liquid was subjected to a search of reaction products by $^{19}$F-NMR. A peak of 2'-deoxy-5,6-dihydro-5-fluoro-6-hydroxyuridine was observed at −7.2 ppm (d, 48 Hz) (standard: $CFCl_3$) and a peak of 2'-deoxy-5,6-dihydro-5-fluoro-6-acetoxyuridine at −8.6 ppm (d, 48 Hz). The proportion of the former peak to the latter peak was 67:33. The pH of the aqueous solution was 5.1.

At temperatures below 40° C. the reaction liquid was concentrated by distilling out water under reduced pressure and then dried almost completely. To the residue 22.4 g (219 mmol) of acetic anhydride was added, and the resultant mixture was stirred at 75° C. for 2.5 hr. Then the liquid was distilled out under reduced pressure, and water and dichloromethane were added. The resultant mixture was allowed to separate into an aqueous layer and a dichloromethane layer dissolving therein the reaction product. The dichloromethane layer was concentrated and dried, and the precipitated product was recrystallized from ethanol to thereby obtain 2.56 g (yield 88.4%) of 2'-deoxy-3',5'-diacetyl-5-fluorouridine (R in the general formula (I) is $CH_3$). Analysis of this product gave the following results.

m.p.: 148°–149° C.

$^1$H-NMR ($CDCl_3$): δ2.15 (s, 6H), 2.2–2.8 (m, 2H); 4.3 (m, 3H), 5.2 (m, 1H), 6.3 (t, 1H); 7.56 (d, 1H, J=6 Hz).

$^{19}$F-NMR ($CDCl_3$): −164.88 ppm (d, J=5.9 Hz); (standard: $CFCl_3$).

EXAMPLES 22–28

In these examples the process of Example 21 was repeated except that in the initial reaction the kind and/or quantity of the fatty acid salt were changed as shown in Table 4. In Examples 27 and 28 the kind of the acid anhydride in the second reaction was also changed as shown in Table 4. In each example a diacyl derivative

REFERENTIAL EXAMPLE

A solution of 15.55 g (0.389 mol) of sodium hydroxide in 200 ml of ino-exchanged water was mixed with 500 ml of methanol and cooled with ice. Then 42.18 g (0.128 mol) of 2'-deoxy-3',5'-diacetyl-5-fluorouridine (R is $CH_3$ in the general formula (I)) was added to the solution under stirring, and stirring was continued at room temperature for 3.5 hr. As a result the reaction liquid became a clear solution. Then 20 g of acetic acid was added to the reaction liquid for neutralization, and the liquid was concentrated under reduced pressure. The solid residue was dissolved by adding 500 ml of water, followed by addition of 100 ml of a cation-exchange resin (IR 120-B), and the solution was left to stand for 1 hr. Then the resin was filtered out, and the addition of the cation-exchange resin and the subsequent treatment were repeated. After that the filtrate was concentrated and dried under reduced pressure. As the result a white solid was obtained. This solid product was recrystallized from ethanol to thereby obtain 24.80 g (yield 78.9%) of 2'-deoxy-5-fluorouridine. The melting point of this product was 149.5°–150.5° C., and the specific rotary power $[\alpha]_D^{25}$ was +37.3° (C=1.06, $H_2O$).

What is claimed is:

1. A process of preparing a diacyl compound of 2'-deoxy-5-fluorouridine represented by the formula (I),

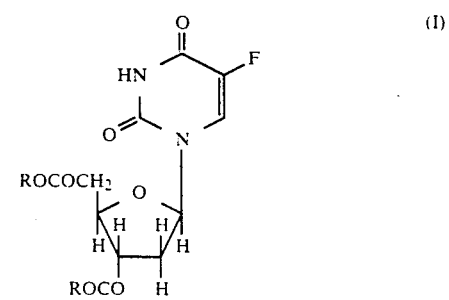

wherein R represents an alkyl group having not more than 20 carbon atoms, the process comprising the steps of:

(i) fluorinating 2'-deoxyuridine in the form of an aqueous solution with fluorine gas at a temperature in the range from 0° C. to room temperature in the presence of a salt of a fatty acid having not more than 4 carbons atoms, the molar ratio of said salt to said 2'-deoxyuridine being not lower than 1, said salt being selected from the group consisting of alkali metal salts, alkaline earth metal salts and ammonium salt; and (ii) reacting a fluorinated intermediate formed at step (i) with a compound represented by the formula (II),

$$R-CO-X \qquad (II)$$

wherein R is as defined above with respect to the formula (I), and X is an acyloxy group represented by $RCO_2$ (where R is the same as R in the formula (II)) or a halogen atom.

2. A process according to claim 1, wherein said molar ratio is from 2 to 5.

3. A process according to claim 1, wherein the concentration of said 2'-deoxyuridine in said aqueous solution is not higher than 10 wt %.

4. A process according to claim 1, wherein said fluorine gas is supplied as a mixed gas consisting of 3-20 mol % of fluorine and the balance of an inactive gas.

5. A process according to claim 1, wherein at step (ii) the molar ratio of said compound to said fluorinated intermediate is not lower than 4.

6. A process according to claim 1, wherein said compound in step (ii) is an acid anhydride selected from the group consisting of acetic anhydride, propionic anhydride, isobutyric anhydride and succinic anhydride.

7. A process according to claim 1, wherein said compound in step (ii) is an acid halide selected from the group consisting of acetyl chloride, acetyl bromide, caprylyl chloride, lauroyl chloride, benzoyl chloride and p-chlorobenzoyl chloride.

8. A process according to claim 1, wherein the reaction at step (ii) is carried out at a temperature in the range from room temperature to the boiling point of said acid anhydrides or halide.

9. A process according to claim 8, wherein said temperature is from 50° to 120° C.

10. A process according to claim 1, wherein the reaction at step (ii) is carried out in the presence of an organic base.

11. A process according to claim 10, wherein said organic base is selected from the group consisting of pyridine, substituted pyridines, N-alkylimidazoles, trialkylamines and N,N-dialkylcarboxylic acid amides.

12. The process of claim 1, wherein the fatty acid is selected from the group consisting of formic acid, acetic acid, propionic acid and butyric acid.

* * * * *